United States Patent
Liu et al.

(10) Patent No.: US 12,426,595 B2
(45) Date of Patent: Sep. 30, 2025

(54) CELL CRYOPRESERVATION SOLUTION AND METHOD FOR CRYOPRESERVING CELLS

(71) Applicants: BOE REGENERATIVE MEDICINE TECHNOLOGY CO., LTD., Beijing (CN); BOE TECHNOLOGY GROUP CO., LTD., Beijing (CN)

(72) Inventors: Donghua Liu, Beijing (CN); Dehua Chang, Beijing (CN); Xuejiao Dong, Beijing (CN); Shuai Liu, Beijing (CN); Yufei Zhao, Beijing (CN); Yang Liu, Beijing (CN); Yuandong Liu, Beijing (CN); Xiaotong Yang, Beijing (CN)

(73) Assignees: BOE REGENERATIVE MEDICINE TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 315 days.

(21) Appl. No.: 17/533,215

(22) Filed: Nov. 23, 2021

(65) Prior Publication Data
US 2022/0264871 A1    Aug. 25, 2022

(30) Foreign Application Priority Data
Jan. 11, 2021    (CN) .......................... 202110031419.3

(51) Int. Cl.
A01N 1/125    (2025.01)
A01N 1/162    (2025.01)
C12N 5/078    (2010.01)

(52) U.S. Cl.
CPC ............. *A01N 1/125* (2025.01); *A01N 1/162* (2025.01); *C12N 5/0634* (2013.01)

(58) Field of Classification Search
CPC .... A01N 1/0221; A01N 1/0284; A01N 1/021; C12N 5/0634; C12N 2500/62; C12N 2523/00
See application file for complete search history.

(56) References Cited

U.S. PATENT DOCUMENTS

2020/0077644 A1 *    3/2020    Church .................. A01N 1/02

FOREIGN PATENT DOCUMENTS

| CN | 102301992 A | 1/2012 |
|---|---|---|
| CN | 102758259 A * | 10/2012 |
| CN | 104082277 A | 10/2014 |
| CN | 105028389 A | 11/2015 |
| CN | 106818710 A | 6/2017 |
| CN | 107711823 A | 2/2018 |
| CN | 108013025 A | 5/2018 |
| CN | 108378021 A | 8/2018 |
| CN | 109892320 A | 6/2019 |
| CN | 109913416 A | 6/2019 |
| CN | 110934134 A | 3/2020 |
| CN | 111849890 A | 10/2020 |
| CN | 112056309 A * | 12/2020 |
| CN | 112167240 A | 1/2021 |
| KR | 20090059289 A | 6/2009 |
| WO | 2007054160 A2 | 5/2007 |

OTHER PUBLICATIONS

Claes F. Högman, Harold T. Meryman, Storage parameters affecting red blood cell survival and function after transfusion, Transfusion Medicine Reviews, vol. 13, Issue 4, pp. 275-296 (Year: 1999).*
Mycielska ME, Mohr MTJ, Schmidt K, Drexler K, Rummele P, Haferkamp S, Schlitt HJ, Gaumann A, Adamski J, Geissler EK. Potential Use of Gluconate in Cancer Therapy. Front Oncol. (Year: 2019).*
D'Amici, Gian Maria, et al. "Red blood cell storage in SAGM and AS3: a comparison through the membrane two-dimensional electrophoresis proteome." Blood Transfusion 10.Suppl 2 (2012): s46. (Year: 2012).*
Xinping et al, "The influence of two different cryopreservation solution on mononuclear cells from cord blood" Journal of Guangxi Medical University, Sep. 2017, 34(9), pp. 1270-1273.
Johnson et al, "Cryopreservation of buffy-coat-derived platelet concentrates in dimethyl sulfoxide and platelet additive solution" Cryobiology, 62 (2011), Jan. 15, 2011, pp. 100-106.
Office Action from Chinese Patent Application No. 202110031419.3 dated Dec. 5, 2022.

* cited by examiner

*Primary Examiner* — Maria G Leavitt
*Assistant Examiner* — Michael Angelo Riga
(74) *Attorney, Agent, or Firm* — Dilworth & Barrese, LLP; Michael J. Musella, Esq.

(57) ABSTRACT

A method for cryopreserving cells, a cell cryopreservation solution and a composition are provided. The method includes: providing a suspension for the cells to be cryopreserved in a cell cryopreservation solution; and cryopreserving the suspension. The cell cryopreservation solution includes dimethyl sulfoxide, plasma, citric acid, sodium citrate, potassium dihydrogen phosphate or sodium dihydrogen phosphate, glucose and adenine.

10 Claims, 2 Drawing Sheets

CELL CRYOPRESERVATION SOLUTION AND METHOD FOR CRYOPRESERVING CELLS

This application claims priority to Chinese Patent Application No. 202110031419.3, filed on Jan. 11, 2021, for all purposes under the U.S. law, the entire disclosure of which is incorporated herein by reference as part of the present application.

TECHNICAL FIELD

The present disclosure is in the field of biotechnology. In particular, the present disclosure relates to a cell cryopreservation solution and a method for cryopreserving cells.

BACKGROUND ART

Human peripheral blood mononuclear cells (PBMCs) are a type of blood leukocytes with a single nucleus, among them are mainly lymphocytes, including a small number of monocytes, plasma cells, etc. These cells play a role of clearing invaders and defending the body in emergencies such as injury, inflammation and infection. In normal conditions, they play a role of clearing senescent and mutated cells in the body on a timely basis and maintaining the balance of cell renewal and clearance in the body. Improving the functions of these cells can optimize the function and status of a body's immune system. Therefore, human peripheral blood mononuclear cells are widely used in clinical applications.

The cryopreservation of human peripheral blood mononuclear cells is one of the key techniques for ensuring successful reinfusion of immune cells. As such, the method of cryopreservation is particularly important. At present, the cryopreservation of human peripheral blood mononuclear cells is carried out at a temperature of −196° C. in liquid nitrogen and it generally requires a cryopreservation period of approximately 30 years. Therefore, the exploration of a method for cryopreservation of human peripheral blood mononuclear cells that is simple, fast and cost-saving and has a long storage time is of great significance for the clinical storage and applications of peripheral blood mononuclear cells. Among them, cryopreservation solutions serve a particularly important function. At present, in addition to commercially available serum-free cryopreservation agents, the preservation solutions for human peripheral blood mononuclear cells used at a deep cryopreservation temperature in liquid nitrogen comprise dimethyl sulfoxide, RPMI1640 medium, and inactivated fetal bovine serum, among others. The formulations and methods of use of various protective agents are different. The preservation effect and storage time for human peripheral blood mononuclear cells are also different. Together with such factors as heterogenous risk in clinical applications, the safety of human peripheral blood mononuclear cells cannot be guaranteed.

SUMMARY

According to at least one embodiment of the disclosure, a method for cryopreserving cells is provided. The method comprises: providing a suspension for the cells to be cryopreserved in a cell cryopreservation solution; and cryopreserving the suspension. The cell cryopreservation solution comprises dimethyl sulfoxide, plasma, citric acid, sodium citrate, potassium dihydrogen phosphate or sodium dihydrogen phosphate, glucose and adenine.

For example, the cell cryopreservation solution comprises one or more of the following features: dimethyl sulfoxide at a volume fraction of 5% to 15%, plasma at a volume fraction of 50% to 90%, citric acid at a mass volume fraction of 0.05% to 0.09%, sodium citrate at a mass volume fraction of 0.40% to 0.70%, potassium dihydrogen phosphate or sodium dihydrogen phosphate at a mass volume fraction of 0.03% to 0.06%, glucose at a mass volume fraction of 0.50% to 1.0%, and adenine at a mass volume fraction of 0.005% to 0.01%.

For example, the cell cryopreservation solution comprises plasma at a volume fraction of 65% to 75%.

For example, the cell cryopreservation solution further comprises calcium gluconate.

For example, the cell cryopreservation solution further comprises calcium gluconate at a mass volume fraction of 0.01% to 0.8%.

For example, the cryopreserving the suspension comprises: subjecting the suspension to a low-temperature standing treatment, wherein the low-temperature standing treatment is carried out at a temperature of −78° C. to −82° C. for a time period within 14 days; and rapid-freezing the suspension after the low-temperature standing treatment, wherein the rapid-freezing treatment is carried out in liquid nitrogen.

For example, the cells to be cryopreserved are human peripheral blood mononuclear cells.

For example, the cells to be cryopreserved are obtained by a process comprising: mixing human peripheral blood with a reagent comprising citric acid at a mass volume fraction of 0.2% to 0.5%, sodium citrate at a mass volume fraction of 2% to 4%, potassium dihydrogen phosphate or sodium dihydrogen phosphate at a mass volume fraction of 0.1% to 0.3%, glucose at a mass volume fraction of 2.5% to 5%, and adenine at a mass volume fraction of 0.02% to 0.05%, wherein the volume ratio of the human peripheral blood to the reagent is 200:(25-30); subjecting the mixed product to density gradient centrifugation to obtain an intermediate cell layer; and resuspending and centrifuging the intermediate cell layer in a new centrifuge tube to obtain the cells to be cryopreserved.

For example, the cell cryopreservation solution is obtained by a process comprising: mixing human peripheral blood with a reagent comprising citric acid at a mass volume fraction of 0.2% to 0.5%, sodium citrate at a mass volume fraction of 2% to 4%, potassium dihydrogen phosphate or sodium dihydrogen phosphate at a mass volume fraction of 0.1% to 0.3%, glucose at a mass volume fraction of 2.5% to 5%, and adenine at a mass volume fraction of 0.02% to 0.05%, wherein the volume ratio of the human peripheral blood to the reagent is 200:(25-30); subjecting the mixed product to density gradient centrifugation treatment to obtain a supernatant; and mixing the supernatant with a predetermined amount of DMSO to obtain the cell cryopreservation solution.

For example, the providing the suspension for the cells to be cryopreserved in a cell cryopreservation solution comprises: mixing human peripheral blood with a reagent comprising citric acid at a mass volume fraction of 0.2% to 0.5%, sodium citrate at a mass volume fraction of 2% to 4%, potassium dihydrogen phosphate or sodium dihydrogen phosphate at a mass volume fraction of 0.1% to 0.3%, glucose at a mass volume fraction of 2.5% to 5%, and adenine at a mass volume fraction of 0.02% to 0.05%, wherein the volume ratio of the human peripheral blood to the reagent is 200:(25-30); subjecting the mixed product to density gradient centrifugation to obtain an intermediate cell layer and a supernatant; resuspending and centrifuging the intermediate cell layer in a new centrifuge tube to obtain the cells to be cryopreserved; mixing the supernatant with a predetermined amount of DMSO to obtain the cryopreservation solution; and resuspending the cells to be cryopreserved in the cryopreservation solution to obtain the suspension.

For example, the density gradient centrifugation is performed within 8 hours after mixing of the human peripheral blood and the reagent.

For example, the method further comprises mixing the supernatant with a predetermined amount of calcium gluconate.

According to at least one embodiment of the disclosure, a cell cryopreservation solution is provided. The cell cryopreservation solution comprises dimethyl sulfoxide, plasma, citric acid, sodium citrate, potassium dihydrogen phosphate or sodium dihydrogen phosphate, glucose and adenine.

For example, the cell cryopreservation solution comprises one or more of the following features: dimethyl sulfoxide at a volume fraction of 5% to 15%, plasma at a volume fraction of 50% to 90%, citric acid at a mass volume fraction of 0.05% to 0.09%, sodium citrate at a mass volume fraction of 0.40% to 0.70%, potassium dihydrogen phosphate or sodium dihydrogen phosphate at a mass volume fraction of 0.03% to 0.06%, glucose at a mass volume fraction of 0.50% to 1.0%, and adenine at a mass volume fraction of 0.005% to 0.01%.

For example, the cell cryopreservation solution comprises plasma at a volume fraction of 65% to 75%.

For example, the cell cryopreservation solution further comprises calcium gluconate.

For example, the cell cryopreservation solution further comprises calcium gluconate at a mass volume fraction of 0.01% to 0.8%.

According to at least one embodiment of the disclosure, a composition is provided. The composition comprises the cell cryopreservation solution as described above and the cells cryopreserved in the cell cryopreservation solution.

For example, the cells and the plasma in the cryopreservation solution are derived from the same organism.

For example, the cells are human peripheral blood mononuclear cells.

DETAILED DESCRIPTION

Unless otherwise defined, all technical and scientific terms used herein have the same meanings as commonly known by those of ordinary skill in the art.

Terms as Used Herein

It should be noted that "mass volume fraction" as described in this application refers to the amount of substance in grams contained in each 100 mL of liquid volume; which can be calculated by dividing the amount of the substance in grams by the volume of the solution that contains the substance.

It should be noted that the "cell cryopreservation base solution" as described in this application refers to the solution that can be used with other material components so as to serve as cell cryopreservation solution. For instance, the "cell cryopreservation base solution" as described in this application can be on this basis and be combined with a predetermined amount of DMSO and/or calcium gluconate so as to obtain the cell cryopreservation solution, which can be used for the cryopreservation of human peripheral blood mononuclear cells.

Cell Cryopreservation Base Solution and its Preparation Method

In one aspect of the present disclosure, the present disclosure provides a cell cryopreservation base solution. According to the embodiments of the present disclosure, the cell cryopreservation base solution comprises plasma at a volume fraction (v/v) of 50% to 90%, citric acid at a mass volume fraction (w/v, g/mL) of 0.05% to 0.09%, sodium citrate at a mass volume fraction (w/v, g/mL) of 0.40% to 0.70%, potassium dihydrogen phosphate or sodium dihydrogen phosphate at a mass volume fraction (w/v, g/mL) of 0.03% to 0.06%, glucose at a mass volume fraction (w/v, g/mL) of 0.50% to 1.0%, and adenine at a mass volume fraction (w/v, g/mL) of 0.005% to 0.01%. According to the embodiments of the present disclosure, the cell cryopreservation base solution in combination with a predetermined amount of dimethyl sulfoxide (DMSO) is suitable for cryopreservation of cells, especially of peripheral blood mononuclear cells. It leads to high survival rate of peripheral blood mononuclear cells following recovery, a large number of proliferated NK cells following recovery, and a high ratio of NK cell differentiation. In particular, the citrate ions in the cell cryopreservation base solution according to the embodiments of the present disclosure, together with the calcium ions in the blood, can form a soluble complex of calcium citrate that is difficult to dissociate, thereby inhibiting the coagulation process and facilitating the subsequent separation of mononuclear cells. Citric acid and sodium citrate can form a buffer pair to adjust and stabilize the pH of the solution. Glucose can provide energy to cells, which is beneficial to preserving the mononuclear cells. Plasma is a nutrient protective agent and comprises various cytokines and nutrients such as serum proteins, inorganic salt ions, and vitamins. It provides human peripheral blood mononuclear cells with the required nutrients, and the serum proteins provide the viscosity of serum that can protect cells from mechanical damage.

According to the embodiments of the present disclosure, it further comprises calcium gluconate at a mass volume fraction (w/v, g/mL) of 0.01% to 0.8%, preferably calcium gluconate at a mass volume fraction of 0.4%. Calcium gluconate complexes the citrate ions in the cell cryopreservation base solution to replenish the calcium ions in the cell cryopreservation base solution, which reduces the damage of the citrate ions to the cells and further increases the survival rate of cryopreserved cells following recovery.

According to the embodiments of the present disclosure, the cells and the plasma are derived from the same organism. Meanwhile, autologous plasma is used for the cryopreservation of the autologous cells. The fact that the autologous plasma does not have heterogeneity avoids the potential safety issue of foreign serum in future clinical applications.

According to the embodiments of the present disclosure, said cells are human peripheral blood mononuclear cells. The cell cryopreservation base solution according to the embodiments of the present disclosure in combination with a predetermined amount of DMSO is especially suitable for cryopreserving human peripheral blood mononuclear cells.

In another aspect of the present disclosure, the present disclosure provides a method for preparing the cell cryopreservation base solution described above. According to the embodiments of the present disclosure, the cell cryopreservation base solution is obtained by: mixing human peripheral blood with reagent to obtain anticoagulated blood, with the volume ratio of human peripheral blood to reagent being 200:(25-30), wherein the reagent comprises citric acid at a mass volume fraction (w/v, g/mL) of 0.2% to 0.5%, sodium citrate at a mass volume fraction (w/v, g/mL) of 2% to 4%, potassium dihydrogen phosphate or sodium dihydrogen phosphate at a mass volume fraction (w/v, g/mL) of 0.1% to 0.3%, glucose at a mass volume fraction (w/v, g/mL) of 2.5% to 5% and adenine at a mass volume fraction (w/v, g/mL) of 0.02% to 0.05%; subjecting the anticoagulated blood to Ficoll-Paque™ PREMIUM density gradient centrifugation treatment to obtain the cell cryopreservation base solution. The method for preparing the cell cryopreservation base solution according to the embodiments of the present disclosure is convenient and easy to use. The resultant cell cryopreservation base solution in combination with a predetermined amount of DMSO is especially suitable for cryopreserving human peripheral blood mononuclear cells.

According to the embodiments of the present disclosure, the obtained supernatant after Ficoll-Paque™ PREMIUM density gradient centrifugation is the cell cryopreservation base solution. The supernatant as described comprises plasma of human peripheral blood and essentially all the reagents. The volume of the plasma separated from the human peripheral blood is approximately half of that of the initial human peripheral blood. For instance, when the volume of the initial human peripheral blood is 200 mL, the volume of the obtained plasma of the human peripheral blood is approximately 100 mL. When the volume of the reagent initially used is 28 mL, all of the 28 mL of the reagent is essentially in the supernatant after centrifugation. Therefore, those of ordinary skill in the art can calculate the content of various substances in the cell cryopreservation base solution based on the content of various substances in the reagent initially used and the dilution ratio. For example, when the volume of the initial human peripheral blood is 200 mL and the volume of the reagent initially used is 28 mL, the content of the various substances in the cell cryopreservation base solution is approximately 28/128 of the content of various substance in the reagent initially used.

According to the embodiments of the present disclosure, the volume ratio of the human peripheral blood and the reagent is 200:(25-30), preferably 50:7. The inventor(s) found that there was an increased risk of blood coagulation when the ratio of the peripheral blood to the reagent was greater than 200:(25-30). Thus, limiting the volume ratio of the human peripheral blood to the reagent to 200:(25-30) is beneficial to lowering the risk of blood coagulation and increasing the separation ratio of human peripheral blood mononuclear cells.

According to the embodiments of the present disclosure, it further comprises mixing the supernatant of the centrifuged product with a predetermined amount of calcium gluconate. According to the specific embodiments of the present disclosure, the cell cryopreservation base solution is the supernatant obtained following the Ficoll-Paque™ PREMIUM density gradient centrifugation. By mixing the supernatant with a predetermined amount of calcium gluconate, the calcium gluconate can be complexed with citrate ions in the cell cryopreservation base solution to replenish the calcium ions therein, thereby reducing the damage of the citrate ions to the cells and further increasing the survival rate of the cryopreserved cells following recovery.

According to the embodiments of the present disclosure, the volume ratio of the anticoagulated blood to the Ficoll-Paque™ PREMIUM is 30:(15-20) for the Ficoll-Paque™ PREMIUM density gradient centrifugation. The inventor(s) found that the amount of the Ficoll-Paque™ PREMIUM used affected the layering of the blood following the centrifugation. When the amount of the Ficoll-Paque™ PREMIUM used was too small, the white film-like layer (intermediate cell layer) after centrifugation may be contaminated by red blood cells. Limiting the volume ratio of the anticoagulated blood to the Ficoll-Paque™ PREMIUM to 30:(15-20) can effectively reduce the possibility of the red blood cell contamination in the white film-like layer after centrifugation.

According to the embodiments of the present disclosure, the volume ratio of the anticoagulated blood to the Ficoll-Paque™ PREMIUM is 2:1.

According to the embodiments of the present disclosure, the Ficoll-Paque™ PREMIUM density gradient centrifugation is performed within 8 hours after mixing the human peripheral blood with the reagent. The inventor(s) found that placing the mixture of the human peripheral blood and the reagent for a period of time before the separation did not affect the ratio of NK cell proliferation following recovery. However, it did significantly affect the fold expansion of the NK cells. As the contact time with the reagent became longer, such as standing for 16 h or 24 h, the fold proliferation of the cells decreased significantly, indicating that the reagent affects the expansion of PBMCs. Performing the density gradient centrifugation within 8 hours after mixing the human peripheral blood with the reagent is beneficial to reducing the toxicity of the reagent to cells and maintaining a high fold proliferation of NK cells after the recovery of cryopreserved human peripheral blood mononuclear cells.

Cell Cryopreservation Solution

In another aspect of the present disclosure, the present disclosure provides a cell cryopreservation solution. According to the embodiments of the present disclosure, the cell cryopreservation solution comprises dimethyl sulfoxide at a volume fraction of 5% to 15% and the cell cryopreservation base solution described above or a cell cryopreservation base solution prepared according to the method described above. According to the embodiments of the present disclosure, the cell cryopreservation solution comprises dimethyl sulfoxide at a volume fraction of 5% to 15% (such as dimethyl sulfoxide at a volume fraction of 5%, 10% or 15%), plasma at a volume fraction of 50% to 90% (such as plasma at a volume fraction of 50%, 55%, 60%, 65%, 70%, 75%, 80%, 85% or 90%), citric acid at a mass volume fraction of 0.05% to 0.09% (such as citric acid at a mass volume fraction of 0.05%, 0.06%, 0.07%, 0.08% or 0.09%), potassium dihydrogen phosphate or sodium dihydrogen phosphate at a mass volume fraction of 0.03% to 0.06% (such as potassium dihydrogen phosphate or sodium dihydrogen phosphate at a mass volume fraction of 0.03%, 0.04%, 0.05% or 0.06%), glucose at a mass volume fraction of 0.50% to 1.0% (such as glucose at a mass volume fraction of 0.50%, 0.60%, 0.70%, 0.80%, 0.90% or 1.0%), and adenine at a mass volume fraction of 0.005% to 0.01% (such as adenine at a mass volume fraction of 0.005%, 0.006%, 0.007%, 0.008%, 0.009% or 0.01%).

Among them, where dimethyl sulfoxide (DMSO) (v/v) of 5% to 15%, DMSO prevents ice crystals from damaging the cells during cryopreservation. When the ratio is less than 5%, the cell damage by ice crystals during cryopreservation cannot be prevented, and when the ratio is greater than 15%, the cells lose too much water and thus die. Where the plasma (v/v) of 50% to 90%, when the ratio is less than 50%, the viscosity of the cryopreservation solution cannot be guaranteed, so that the cells cannot be protected from mechanical damage. Where the citric acid (w/v) of 0.05% to 0.09% and the sodium citrate (w/v) of 0.40% to 0.70%, the citrate ions complex calcium ions in peripheral blood to form calcium citrate. When the content is low, blood coagulates due to the inability to completely complex all the calcium ions in the peripheral blood. In addition, citric acid and sodium citrate form a buffer pair, which can adjust and stabilize the pH of the solution. When the content is too high, the pH of the solution cannot be guaranteed, which can cause the death of cells. Where the potassium dihydrogen phosphate or sodium dihydrogen phosphate (w/v) of 0.03% to 0.06%, it provides phosphate for cell metabolism.

The cell cryopreservation solution according to the embodiments of the present disclosure uses simple formulation and affordable raw materials. It is easy to use, while it can effectively protect human peripheral blood mononuclear cells from being damaged during cryopreservation with high safety and little harm to the cells. It can increase the survival rate of human mononuclear cells to 80% following recovery. Following recovery and induced proliferation of NK cells, there will be a large number of cell proliferations and a high ratio of NK cell differentiation, which ensures the physiological functions and biological properties of human mononuclear cells following recovery.

Method for Cryopreserving Cells

In yet another aspect of the present disclosure, the present disclosure provides a method for cryopreserving cells. According to the embodiments of the present disclosure, the method comprises suspending the cells to be cryopreserved with the cell cryopreservation solution described above. The method for cryopreserving cells according to the embodiments of the present disclosure does little harm to the cells and can improve the survival rate of the cryopreserved cells and the fold proliferation of induced cells following recovery.

According to the embodiments of the present disclosure, the method further comprises subjecting the suspension for cells to be cryopreserved to a low-temperature standing treatment, which is carried out at −78° C. to −82° C. for 1 to 14 days, and rapid-freezing the suspension after the low-temperature standing treatment, wherein the rapid-freezing treatment is carried out in liquid nitrogen. The inventor(s) found that so long as the low-temperature standing time was less than 14 days, there was no significant difference in cell survival rate after recovery. However, when the low-temperature standing treatment exceeded 14 days, such as 21 days, the cell survival rate decreased significantly following recovery.

According to the embodiments of the present disclosure, the cells to be cryopreserved are human peripheral blood mononuclear cells and are obtained by: mixing the human peripheral blood with a reagent to obtain anticoagulated blood. The volume fraction of the human peripheral blood to the reagent is 200:(25-30), preferably 200:28. Among them, the reagent comprises citric acid at a mass volume fraction of 0.2% to 0.5%, sodium citrate at a mass volume fraction of 2% to 4%, potassium dihydrogen phosphate or sodium dihydrogen phosphate at a mass volume fraction of 0.1% to 0.3%, glucose at a mass volume fraction of 2.5% to 5%, and adenine at a mass volume fraction of 0.02% to 0.05%; subjecting the anticoagulated blood to Ficoll-Paque™ PREMIUM density gradient centrifugation treatment to obtain an intermediate cell layer; resuspending and centrifuging the intermediate cell layer in a new centrifuge tube to obtain the cells to be cryopreserved. At the same time of obtaining the cells to be cryopreserved, the supernatant resulting from the Ficoll-Paque™ PREMIUM density centrifugation can be used as the cell cryopreservation base solution for cryopreservation of the cells to be cryopreserved. Human autologous plasma, as a component of the cell cryopreservation solution, has no heterogeneity, which avoids the potential safety issue of foreign serum in future clinical applications. And it is a byproduct of human peripheral blood separation and thus is easy to obtain and cost-effective.

According to the embodiments of the present disclosure, the Ficoll-Paque™ PREMIUM density gradient centrifugation is performed within 8 hours after mixing human peripheral blood with reagent. The inventor(s) found that performing the centrifugation within 8 hours after mixing human peripheral blood with reagent was beneficial to maintaining a high fold proliferation of NK cells following the recovery of peripheral blood mononuclear cells.

In yet another aspect of the present disclosure, the present disclosure provides a method for cryopreserving cells. According to the embodiments of the present disclosure, the method comprises: mixing human peripheral blood with a reagent to obtain anticoagulated blood, preferably with the standing time after the mixing not exceeding 8 hours. The volume ratio of the human peripheral blood to the reagent is 200:(25-30). Among them, the reagent comprises citric acid at a mass volume fraction (w/v, g/mL) of 0.2% to 0.5%, sodium citrate at a mass volume fraction (w/v, g/mL) of 2% to 4%, potassium dihydrogen phosphate or sodium dihydrogen phosphate at a mass volume fraction (w/v, g/mL) of 0.1% to 0.3%, glucose at a mass volume fraction (w/v, g/mL) of 2.5% to 5%, and adenine at a mass volume fraction (w/v, g/mL) of 0.02% to 0.05%. The reagents can be self-prepared or purchased. The anticoagulated blood is subjected to Ficoll-Paque™ PREMIUM density gradient centrifugation to obtain a supernatant and an intermediate cell layer. The supernatant constitutes the cell cryopreservation base solution and the intermediate cell layer is resuspended and centrifuged in a new centrifuge tube to obtain the cells to be cryopreserved. The cell cryopreservation base solution is mixed with DMSO to obtain a cell cryopreservation solution, with the volume fraction of the DMSO being 5% to 15% in the cell cryopreservation solution. The cells to be cryopreserved are resuspended using the cell cryopreservation solution. The resuspended solution for the cells to be cryopreserved is subjected to a low-temperature standing treatment, which is preferably carried out at −78° C. to −82° C. for 1 to 14 days. The suspension for cells to be cryopreserved is rapid-frozen after the low-temperature standing treatment for the purpose of cell cryopreservation, wherein the rapid-freezing treatment is performed in liquid nitrogen. The method according to the embodiments of the present disclosure is suitable for cryopreserving human peripheral blood mononuclear cells and can effectively protect human peripheral blood mononuclear cells from freezing-related damage with high safety and little harm to the cells. It can increase the survival rate of human mononuclear cells following recovery. Following recovery and induced proliferation of NK cells, there will be a large number of cell proliferations and a high ratio of NK cell differentiation, which ensures the physiological functions and biological properties of human mononuclear cells following recovery.

The following examples are provided to further illustrate the present invention. It should be understood that these examples are only used to illustrate the present invention and are not to limit the scope of the present invention.

The experimental methods that do not indicate specific conditions in the following examples can be carried out according to the conventional conditions of this type of reaction or according to the conditions recommended by the manufacturer.

The experimental materials and reagents used in the following examples are commercially available unless otherwise specified.

Reagent I contains 3.27 g of citric acid ($C_6H_8O_7 \cdot H_2O$), 26.3 g of sodium citrate ($C_6H_5Na_3O_7 \cdot 2H_2O$), 2.22 g of sodium dihydrogen phosphate ($NaH_2PO_4 \cdot H_2O$), 31.9 g of glucose ($C_6H_{12}O_6 \cdot H_2O$) and 0.275 g of adenine ($C_5H_5N_5$) per 1000 mL.

The molecular formula of calcium gluconate in a 10% calcium gluconate injectable solution is $C_{12}H_{22}CaO_{14} \cdot H_2O$, with chemical name of calcium D-gluconate monohydrate.

EXAMPLE 1

1. Mixing 200 mL of human peripheral blood with 25-30 mL of reagent I to form anticoagulated blood. Preferably, the volume ratio of the peripheral blood to the blood reagent I is 50:7.

2. Adding 15-20 mL, preferably 15 mL, of Ficoll-Paque™ PREMIUM to the bottom of a 50 mL sterile tube.

3. Taking 30 mL of the anticoagulated blood and slowly adding it to the 50 mL sterile centrifuge tube without destroying the Ficoll-Paque™ PREMIUM interface. Repeating steps 2 and 3 until all 228 mL of the anticoagulated blood is added to different 50 mL sterile tubes, which are then centrifuged at 800 g for 20 minutes.

4. After centrifugation, taking the transparent plasma mixture from the upper layer, transferring it to a new centrifuge tube, inactivating it in a 56° C. water bath for 30 minutes, transferring it at −20° C. and allowing it stand for 5 minutes, and then subjecting it to centrifugation at 3000 g for 15 minutes. Thereafter, aspirating its supernatant and storing the supernatant in a new cryopreservation tube. By mixing to obtain a mixture of human autologous plasma and reagent I for cryopreservation.

5. Adding DMSO to the mixture of human autologous plasma and reagent I for cryopreservation to make dimethyl sulfoxide (DMSO) (v/v) of 5% to 15% in order to obtain a cell cryopreservation solution. It is calculated that the cell cryopreservation solution comprises dimethyl sulfoxide at a volume fraction of 5% to 15%, plasma at a volume fraction of 50% to 90%, citric acid at a mass volume fraction of 0.05% to 0.09%, sodium citrate at a mass volume fraction of 0.40% to 0.70%, potassium dihydrogen phosphate or sodium dihydrogen phosphate at a mass volume fraction of 0.03% to 0.06%, glucose at a mass volume fraction of 0.50% to 1.0%, and adenine at a mass volume fraction of 0.005% to 0.01%.

6. Taking the intermediate cell layer, and transferring it to a new centrifuge tube. Adding 30 mL of PBS to every 15 mL of the cell suspension, which is then centrifuged at 800 g for 7 minutes. Following discarding the supernatant, adding another 30 mL of PBS for resuspension of cells, performing centrifugation at 800 g for 7 minutes, and discarding the supernatant.

7. Preparing a suspension for cell cryopreservation solution at a density of $1 \times 10^7$ cells resuspended in 1 mL of cell cryopreservation solution.

8. Adding 1 mL of the suspension for cell cryopreservation solution to each 2 mL cryopreservation tube, and placing it in a programmed cooler for cooling and cryopreservation.

9. After placing the programmed cooler at −80° C. overnight, transferring the cryopreservation tubes to liquid nitrogen for permanent storage.

EXAMPLE 2

1. Mixing 200 mL of human peripheral blood with 25-30 mL of reagent I to form anticoagulated blood. Preferably, the volume ratio of the peripheral blood to the reagent I is 50:7.

2. Adding 15-20 mL, preferably 15 mL, of Ficoll-Paque™ PREMIUM to the bottom of a 50 mL sterile tube.

3. Take 30 mL of the anticoagulated blood and slowly adding it to the 50 mL sterile centrifuge tube without destroying the Ficoll-Paque™ PREMIUM interface. Repeating steps 2 and 3 until all 228 mL of the anticoagulated blood is added to different 50 mL centrifuge tubes, which are then centrifuged at 800 g for 20 minutes.

4. After centrifuging, taking the transparent plasma mixture of the upper layer, transferring it to a new centrifuge tube, inactivating it in a 56° C. water bath for 30 minutes, transferring it at −20° C. and allowing it stand for 5 minutes, and then subjecting it to centrifugation at 3000 g for 15 minutes. Thereafter, aspirating its supernatant, storing the supernatant in a new cryopreservation tube, and adding a calcium gluconate injectable solution (10%, g/mL) of 0.01% to 8% (v/v) by volume ratio. By mixing to obtain a mixture of human autologous plasma and reagent I for cryopreservation.

5. Adding DMSO to the mixture of human autologous plasma and reagent I for cryopreservation to make dimethyl sulfoxide (DMSO) (v/v) of 5% to 15% in order to obtain a cell cryopreservation solution. It is calculated that the cell cryopreservation solution comprises dimethyl sulfoxide at a volume fraction of 5% to 15%, plasma at a volume fraction of 50% to 90%, calcium gluconate at a mass volume fraction of 0.01% to 0.8%, citric acid at a mass volume fraction of 0.05% to 0.09%, sodium citrate at a mass volume fraction of 0.40% to 0.70%, potassium dihydrogen phosphate or sodium dihydrogen phosphate at a mass volume fraction of 0.03% to 0.06%, glucose at a mass volume fraction of 0.50% to 1.0%, and adenine at a mass volume fraction of 0.005% to 0.01%.

6. Taking the intermediate cell layer, and transferring it to a new centrifuge tube. Adding 30 mL of PBS to every 15 mL of cell suspension, which is then centrifuged at 800 g for 7 minutes. Following discarding the supernatant, adding another 30 mL of PBS for resuspension of cells, performing centrifugation at 800 g for 7 minutes, and discarding the supernatant.

7. Preparing a suspension for cell cryopreservation solution at a density of $1 \times 10^7$ cells resuspended in 1 mL of cell cryopreservation solution.

8. Adding 1 mL of the suspension for cell cryopreservation solution to each 2 mL cryopreservation tube, and placing it in a programmed cooler for cooling and cryopreservation.

9. After placing the programmed cooler at −80° C. overnight, transferring the cryopreservation tubes to liquid nitrogen for permanent storage.

EXAMPLE 3

In this example, the protection of the biological properties of mononuclear cells by the cryopreservation solution obtained in Example 1 is determined by the survival rate of the recovered mononuclear cells and the ratio of NK cells proliferation and differentiation following recovery.

The experimental method is as follows.

Taking out cells that had been cryopreserved in liquid nitrogen for 0.5 months, placing them in a 37° C. water bath, vortexing until cell suspension melts, centrifuging, washing twice with PBS and calculating the survival rate.

The survival rate of mononuclear cells following recovery is calculated (the cryopreservation density of $1.0 \times 10^7$ cells/mL) after 0.5 months of cryopreservation using the cell cryopreservation solution obtained in Example 1 and comparison cell cryopreservation solutions. The results are shown in Table 1.

TABLE 1

| Number | Volunteer A | Volunteer B | Volunteer C | Volunteer D | Volunteer E |
|---|---|---|---|---|---|
| Cryopreservation solution of Example 1 | 81.12% | 83.12% | 91.44% | 90.12% | 86.75% |
| Traditional cryopreservation solution (10% DMSO + 90% fetal bovine serum) | 80.55% | 78.73% | 80.77% | 82.97% | 82.04% |
| Commercially available cell cryopreservation solution I | 77.98% | 74.81% | 84.66% | 83.92% | 75.70% |
| Commercially available cell cryopreservation solution II | 87.96% | 74.09% | 82.38% | 86.80% | 84.79% |
| Commercially available cell cryopreservation solution III | 88.16% | 81.43% | 85.42% | 89.35% | 87.16% |
| Commercially available cell cryopreservation solution IV | 84.63% | 76.27% | 89.46% | 91.89% | 87.16% |

It can be seen from Table 1 that after cryopreserving the No. A, B, C, D and E mononuclear cells using the method in Example 1 for 0.5 months, the survival rate of recovered cells was higher than that using the traditional cryopreservation solution, and was comparable to that using the commercially available cell cryopreservation solutions. The mononuclear cells that were cryopreserved using the method in Example 1 were not contaminated by visible foreign matters, bacteria, fungi, endotoxins, and mycoplasma following recovery.

Further by NK cells induced proliferation experiment, the ratio of induced differentiation into NK cells were detected after human peripheral blood mononuclear cells were recovered following cryopreservation of 0.5 months on day 15 of induced proliferation and differentiation of NK cells. The results are shown in Table 2 and FIG. 1.

TABLE 2

| Number | Volunteer 1 | Volunteer 2 | Volunteer 3 | Volunteer 4 | Volunteer 5 | Volunteer 6 |
|---|---|---|---|---|---|---|
| Cryopreservation solution of Example 1 | 91.8% | 81.6% | 73.6% | 91.9% | 68.5% | 81.2% |
| Traditional cryopreservation solution (10% DMSO + 90% fetal bovine serum) | 86.7% | 67.4% | 63.5% | 87.6% | 60.2% | 72.4% |
| Commercially available cell cryopreservation solution I | 93.0% | 81.7% | 79.2% | 76.9% | 78.3% | 85.4% |
| Commercially available cell cryopreservation solution II | 78.5% | 69.6% | 63.9% | 91.0% | 66.6% | 83.1% |
| Commercially available cell cryopreservation solution III | 90.2% | 66.6% | 65.3% | 91.5% | 79.7% | 87.5% |
| Commercially available cell cryopreservation solution IV | 62.2% | 60.9% | 64.1% | 90.8% | 55.8% | 61.9% |

Figure 1:
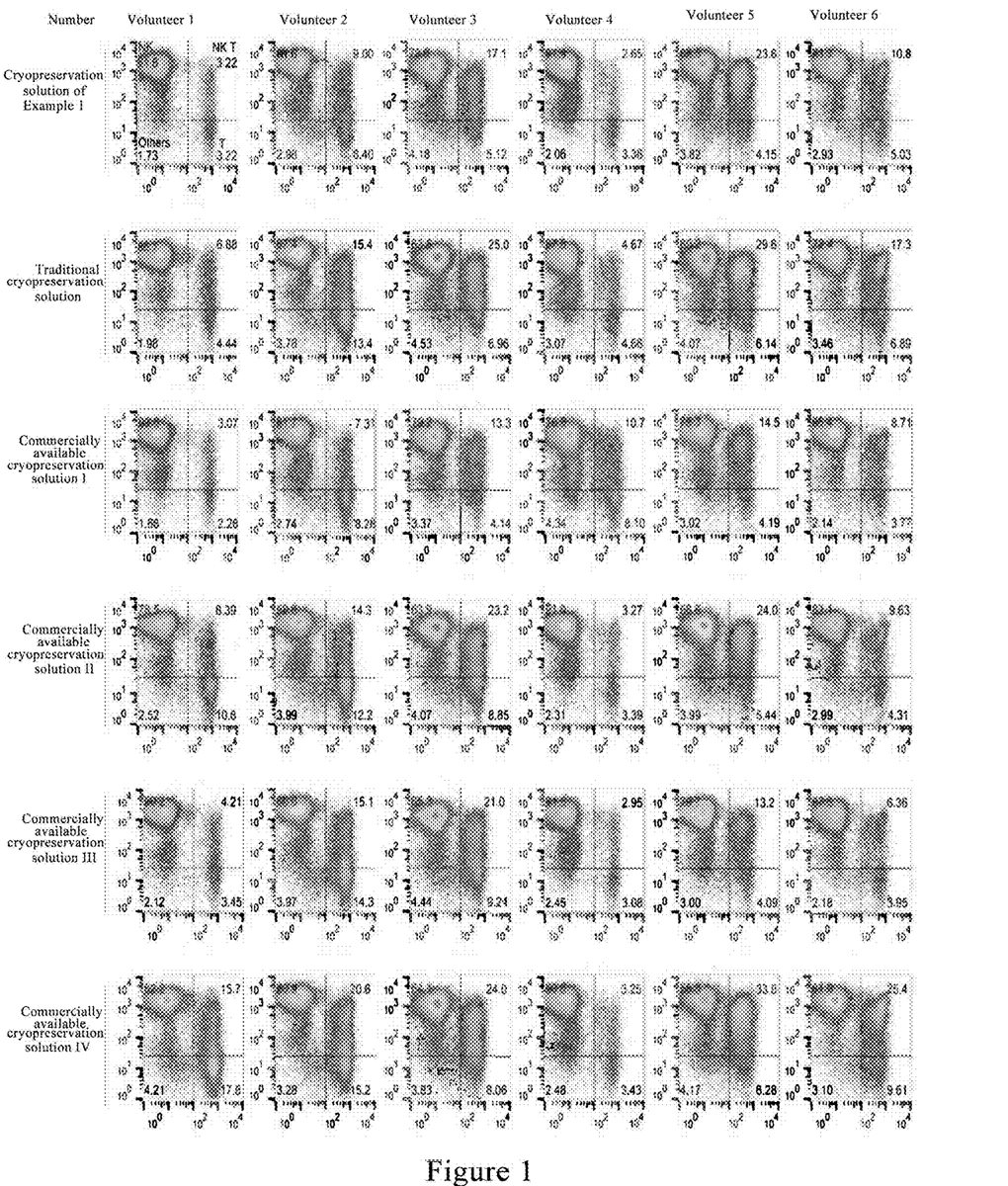
FIG. 1 illustrates the results of a flow cytometry assay of the NK cells induced differentiation after recovery following cryopreservation of human peripheral blood mononuclear cells according to the examples of the present disclosure.

It can be seen from Table 2 and FIG. 1 that after the recovery of the mononuclear cells that were cryopreserved using the method in Example 1 and re-expansion of the NK cells, the ratio of induced differentiation into NK cells can exceed 65%. The ratio of proliferation and differentiation of NK cells increased significantly as compared to that using the traditional cryopreservation solution and was comparable to that using commercially available cell cryopreservation solutions.

It can be illustrated by the examples described above that the cryopreservation solution for human peripheral blood mononuclear cells of the present disclosure can be employed to preserve human peripheral blood mononuclear cells for a long period.

EXAMPLE 4

This example explores the effect of the standing time after mixing human peripheral blood with reagent I on PBMCs in peripheral blood.

Figure 2:
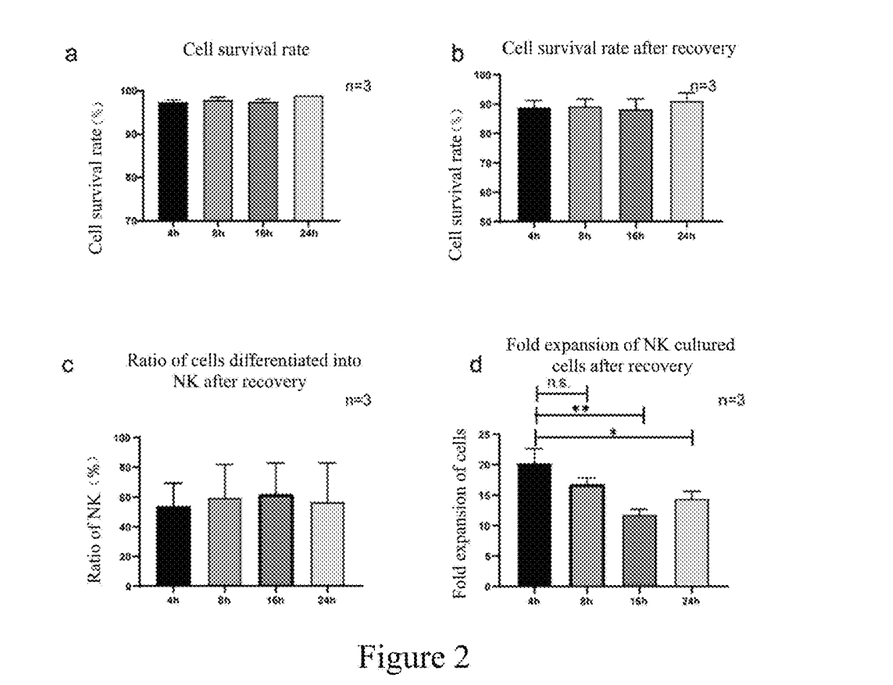
FIG. 2 illustrates the effect of the standing time after mixing the human peripheral blood with the reagent I on PBMCs in the peripheral blood according to the examples of the present disclosure.

In this study, fresh human blood collected from a blood collection bag was mixed with reagent I and was placed at a storage temperature of 10° C. for 4 h, 8 h, 16 h, and 24 h, respectively. Then separation of PBMCs was performed, followed by cell counting and detection of cell survival rate. The detection results show that there was no significant difference in cell survival rate after storage in a 10° C. environment for 4 h, 8 h, 16 h and 24 h (FIG. 2a).

Subsequently, these cells in this study were cryopreserved using the method in Example 1 and the survival rate of the recovered cells were detected. The experimental results show that there was no significant difference in cell survival rate after recovery, which indicates that reagent I has no effect on the survival rate of PBMCs after recovery following cryopreservation (FIG. 2b).

Finally, this study explored the effect of the standing time after mixing human peripheral blood with reagent I on the functionality of NK cells expanded and cultured in vitro. The results show that after mixing fresh peripheral blood with reagent I, standing for 4 h, 8 h, 16 h, and 24 h followed by separation did not affect cryopreserving cells using the method in Example 1 or the expansion ratio of NK cells after recovery (FIG. 2c). However, it did significantly affect the fold expansion of NK cells after recovery following cryopreservation. As the time of contact with reagent I was prolonged, the fold proliferation of cells decreased significantly, which indicates that reagent I affects the expansion of PBMCs (FIG. 2d).

EXAMPLE 5

This example explores the effect of the low-temperature standing time of the resuspended solution for the cells to be cryopreserved on the cells after resuspending the cells in the cell cryopreservation solution in Example 1.

In the process of storing cells, PBMCs separated from peripheral blood usually need to be cooled at −80° C. (low-temperature standing treatment) before being cryopreserved in liquid nitrogen. At the same time, quality inspectors need to conduct related quality inspection such as sterility and endotoxin on PBMCs. Only qualified samples can be transferred to −196° C. gas phase liquid nitrogen tank for formal preservation. Therefore, it is very important to explore the effect of storage time at −80° C. on PBMCs. In order to verify the effect of the storage time of PBMCs in a −80° C. refrigerator on cell survival rate, PBMCs separated from fresh blood were placed at −80° C. for 2, 7, 14 and 21 days, respectively, and were then transferred to liquid nitrogen for cryopreservation. After being cryopreserved in liquid nitrogen for one month, the cells were recovered and were detected for cell survival rate and the proliferation ability of the peripheral blood NK cells.

Figure 3:
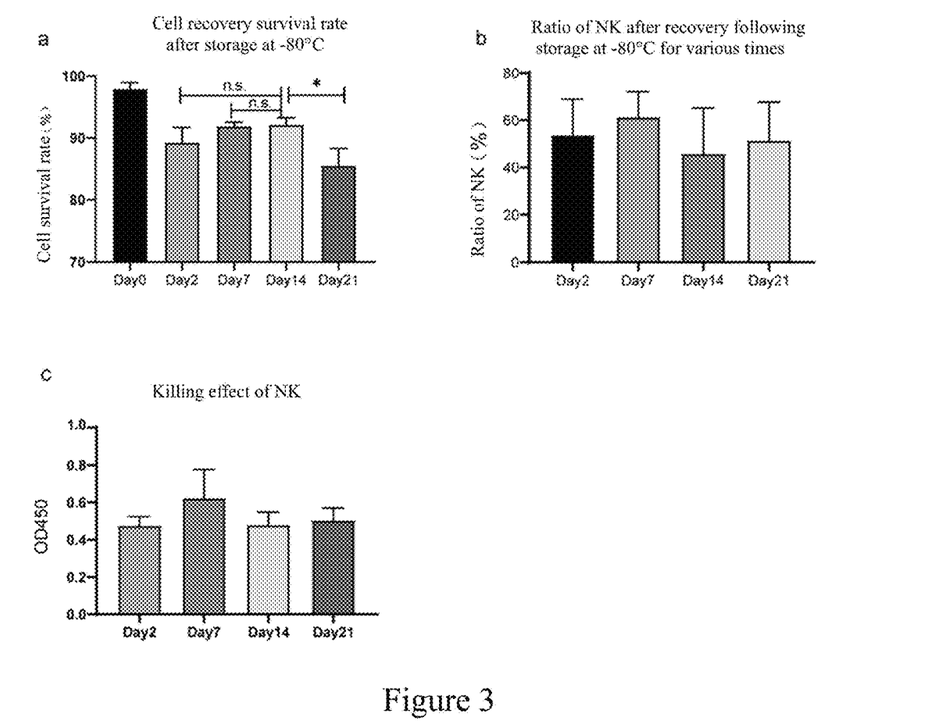
FIG. 3 illustrates the effect of the low-temperature standing time of the resuspension for the cells to be cryopreserved on the cells according to the examples of the present disclosure.

The experimental results show that there was no significant difference in the survival rate of PBMCs following recovery after the cell resuspension was placed at −80° C. for 2, 7, and 14 days, but the cell survival rate following PBMC recovery decreased significantly after storage at −80° C. for 21 days (FIGS. 3a-c).

Unless otherwise defined, all technical and scientific terms used herein have the same meanings as commonly known by those of ordinary skill in the art.

All the features disclosed in this specification can be combined in any combination. Each feature disclosed in this specification can be replaced by an alternative feature having the same, equivalent or similar purpose. Therefore, unless otherwise expressly stated, each feature disclosed herein is merely an example of a series of equivalent or similar features.

Based on the above description, those skilled in the art can easily ascertain the basic features of the present invention and, without departing from the spirit and scope of the present invention, can make various changes and modifications to the present invention so as to adapt it to various uses and conditions. Therefore, other examples are also within the scope of the appended claims.

What is claimed is:

1. A method for cryopreserving human peripheral blood mononuclear cells, comprising:
   providing a suspension for the human peripheral blood mononuclear cells in a cell cryopreservation solution; and
   cryopreserving the suspension,
   wherein the cell cryopreservation solution comprises:
   dimethyl sulfoxide at a volume fraction of 5% to 15%,
   plasma at a volume fraction of 50% to 90%,
   citric acid at a mass volume fraction of 0.05% to 0.09%,
   sodium citrate at a mass volume fraction of 0.40% to 0.70%,
   potassium dihydrogen phosphate or sodium dihydrogen phosphate at a mass volume fraction of 0.03% to 0.06%,
   glucose at a mass volume fraction of 0.50% to 1.0%,
   adenine at a mass volume fraction of 0.005% to 0.01%, and
   calcium gluconate at a mass volume fraction of 0.01% to 0.8%.

2. The method of claim 1, wherein the cell cryopreservation solution comprises plasma at a volume fraction of 65% to 75%.

3. The method of claim 1, wherein the cryopreserving the suspension comprises:
   subjecting the suspension to a low-temperature standing treatment, wherein the low-temperature standing treatment is carried out at a temperature of −78° C. to −82° C. for a time period within 14 days; and
   rapid-freezing the suspension after the low-temperature standing treatment, wherein the rapid-freezing treatment is carried out in liquid nitrogen.

4. The method of claim 1, wherein the human peripheral blood mononuclear cells are obtained by a process comprising:
   mixing human peripheral blood with a reagent comprising citric acid at a mass volume fraction of 0.2% to 0.5%, sodium citrate at a mass volume fraction of 2% to 4%, potassium dihydrogen phosphate or sodium dihydrogen phosphate at a mass volume fraction of 0.1% to 0.3%, glucose at a mass volume fraction of 2.5% to 5%, and adenine at a mass volume fraction of 0.02% to 0.05%, wherein the volume ratio of the human peripheral blood to the reagent is 200:25 to 200:30; subjecting the mixed product to density gradient centrifugation to obtain an intermediate cell layer; and
   resuspending and centrifuging the intermediate cell layer in a new centrifuge tube to obtain the human peripheral blood mononuclear cells.

5. The method of claim 1, wherein the cell cryopreservation solution is obtained by a process comprising:
   mixing human peripheral blood with a reagent comprising citric acid at a mass volume fraction of 0.2% to 0.5%, sodium citrate at a mass volume fraction of 2% to 4%, potassium dihydrogen phosphate or sodium dihydrogen phosphate at a mass volume fraction of 0.1% to 0.3%, glucose at a mass volume fraction of 2.5% to 5%, and adenine at a mass volume fraction of 0.02% to 0.05%, wherein the volume ratio of the human peripheral blood to the reagent is 200:25 to 200:30;
   subjecting the mixed product to density gradient centrifugation treatment to obtain a supernatant; and
   mixing the supernatant with a predetermined amount of calcium gluconate and dimethyl sulfoxide to obtain the cell cryopreservation solution.

6. The method of claim 1, wherein the providing the suspension for the human peripheral blood mononuclear cells in a cell cryopreservation solution comprises:
- mixing human peripheral blood with a reagent comprising citric acid at a mass volume fraction of 0.2% to 0.5%, sodium citrate at a mass volume fraction of 2% to 4%, potassium dihydrogen phosphate or sodium dihydrogen phosphate at a mass volume fraction of 0.1% to 0.3%, glucose at a mass volume fraction of 2.5% to 5%, and adenine at a mass volume fraction of 0.02% to 0.05%, wherein the volume ratio of the human peripheral blood to the reagent is 200:25 to 200:30;
- subjecting the mixed product to density gradient centrifugation to obtain an intermediate cell layer and a supernatant;
- resuspending and centrifuging the intermediate cell layer in a new centrifuge tube to obtain the human peripheral blood mononuclear cells;
- mixing the supernatant with a predetermined amount of calcium gluconate and dimethyl sulfoxide to obtain the cryopreservation solution; and
- resuspending the human peripheral blood mononuclear cells in the cryopreservation solution to obtain the suspension.

7. The method of claim 6, wherein the density gradient centrifugation is performed within 8 hours after the mixing of the human peripheral blood and the reagent.

8. The method of claim 6, wherein the method further comprises mixing the supernatant with a predetermined amount of calcium gluconate.

9. A composition, comprising a human peripheral blood mononuclear cell cryopreservation solution and human peripheral blood mononuclear cells cryopreserved in the cell cryopreservation solution, wherein the human peripheral blood mononuclear cell cryopreservation solution comprises:
- dimethyl sulfoxide at a volume fraction of 5% to 15%,
- plasma at a volume fraction of 50% to 90%,
- citric acid at a mass volume fraction of 0.05% to 0.09%,
- sodium citrate at a mass volume fraction of 0.40% to 0.70%,
- potassium dihydrogen phosphate or sodium dihydrogen phosphate at a mass volume fraction of 0.03% to 0.06%,
- glucose at a mass volume fraction of 0.50% to 1.0%,
- adenine at a mass volume fraction of 0.005% to 0.01%, and
- calcium gluconate a mass volume fraction of 0.01% to 0.8%.

10. The composition of claim 9, wherein the human peripheral blood mononuclear cells and the plasma in the cryopreservation solution are derived from the same organism.

* * * * *